United States Patent
Wang et al.

(10) Patent No.: US 10,633,329 B2
(45) Date of Patent: Apr. 28, 2020

(54) METHOD FOR PREPARING LISINOPRIL INTERMEDIATE

(71) Applicants: ZHEJIANG HUAHAI PHARMACEUTICAL CO., LTD., Taizhou (CN); ZHEJIANG HUAHAI TIANCHENG PHARMACEUTICALS CO., LTD., Taizhou (CN); ZHEJIANG HUAHAI LICHENG PHARMACEUTICALS CO., LTD., Taizhou (CN)

(72) Inventors: Songqing Wang, Taizhou (CN); Peng Dong, Taizhou (CN); Yang Zheng, Taizhou (CN); Quanjun Li, Taizhou (CN)

(73) Assignees: ZHEJIANG HUAHAI PHARMACEUTICAL CO., LTD., Taizhou, Zhejiang (CN); ZHEIJIANG HUAHAI TIANCHENG PHARMACEUTICALS CO., LTD., Taizhou, Zhejiang (CN); ZHEJIANG HUAHAI LICHENG PHARMACEUTICALS CO., LTD., Taizhou, Zhejiang (CN)

( * ) Notice: Subject to any disclaimer, the term of this patent is extended or adjusted under 35 U.S.C. 154(b) by 0 days.

(21) Appl. No.: 16/461,589

(22) PCT Filed: Nov. 17, 2017

(86) PCT No.: PCT/CN2017/111524
§ 371 (c)(1),
(2) Date: May 16, 2019

(87) PCT Pub. No.: WO2018/090963
PCT Pub. Date: May 24, 2018

(65) Prior Publication Data
US 2019/0367444 A1    Dec. 5, 2019

(30) Foreign Application Priority Data

Nov. 17, 2016 (CN) .......................... 2016 1 1011630

(51) Int. Cl.
| | |
|---|---|
| C07C 227/08 | (2006.01) |
| C07C 303/00 | (2006.01) |
| C07C 303/28 | (2006.01) |
| C07C 229/36 | (2006.01) |

(52) U.S. Cl.
CPC .......... C07C 227/08 (2013.01); C07C 303/28 (2013.01); *C07C 229/36* (2013.01)

(58) Field of Classification Search
CPC ............................ C07C 227/08; C07C 303/28
See application file for complete search history.

(56) References Cited

U.S. PATENT DOCUMENTS 4,925,969 A * 5/1990 Takahashi ............. C07C 227/08
560/38

FOREIGN PATENT DOCUMENTS

| CN | 101239923 A | 8/2008 |
| CN | 102617704 A | 8/2012 |
| WO | 2005010028 A1 | 2/2005 |

OTHER PUBLICATIONS

International Search Report for International Application No. PCT/CN2017/111524, dated Feb. 9, 2018, 2 pages.

* cited by examiner

*Primary Examiner* — Sikarl A Witherspoon
(74) *Attorney, Agent, or Firm* — Armstrong Teasdale LLP

(57) ABSTRACT

A method for preparing a lisinopril intermediate is provided. The method includes: treating (R)-hydroxy-4-phenylbutyrate with sulfonyl chloride in an organic solvent in the presence of a base to obtain a solution of sulfonate; reacting the obtained solution with a salt of trifluoroacetyl lysine; and obtaining a $N^2$-[1-(S)-alkoxycarbonyl-3-phenylpropyl]-$N^6$-trifluoroacetyl-L-lysine by separating after the reaction is completed. The method provided has a shorter synthesis route, is easy to operate, has a low cost, and is suitable for industrial production.

20 Claims, 1 Drawing Sheet

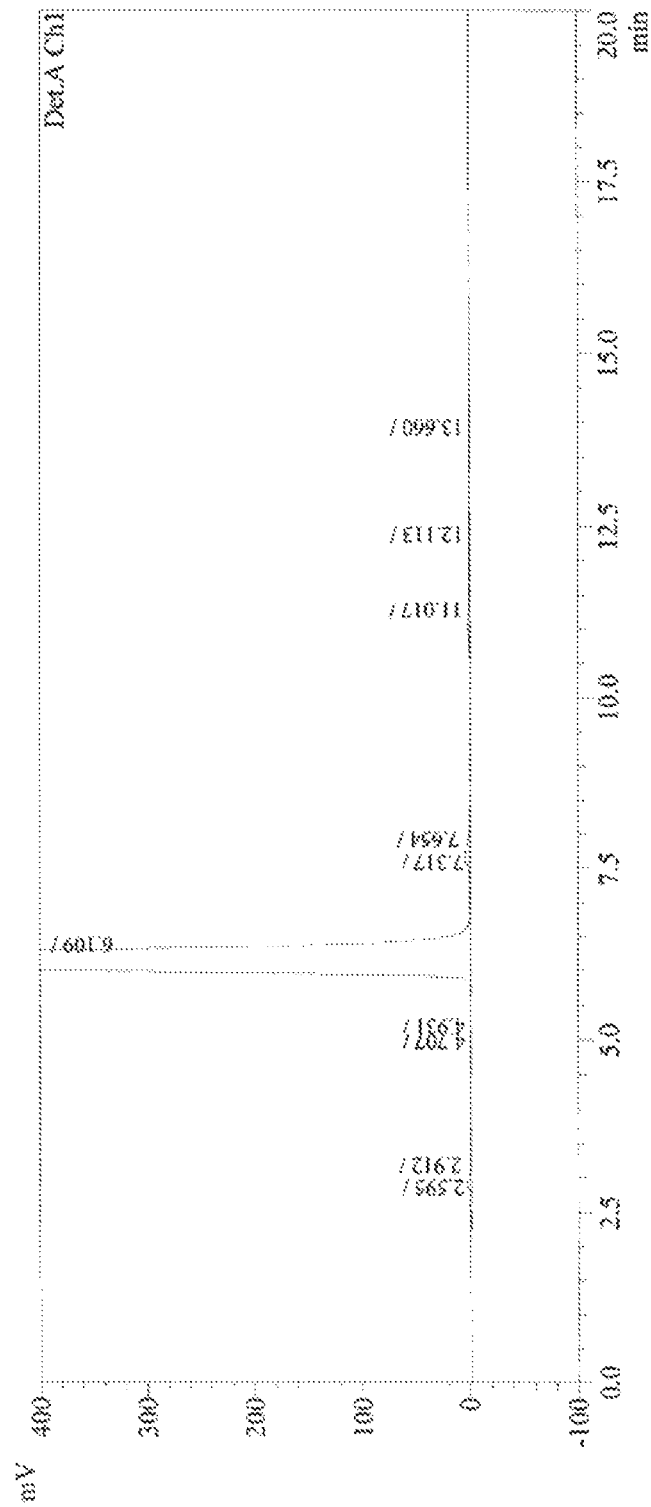

METHOD FOR PREPARING LISINOPRIL INTERMEDIATE

CROSS-REFERENCE TO RELATED APPLICATIONS

This application is a U.S. National Phase Application of PCT/CN2017/111524, filed Nov. 17, 2017, which claims the benefit of priority to CN Application No. 201611011630.4, filed Nov. 17, 2016, the contents of which are hereby expressly incorporated by reference in their entirety.

TECHNICAL FIELD

The present invention relates to the field of pharmaceutical and chemical industry, specifically to a method for preparing lisinopril intermediate.

TECHNICAL BACKGROUND

Lisinopril is a third-generation long-acting angiotensin-converting enzyme (ACE) inhibitor developed by Merck, U.S., clinically used for the treatment of essential hypertension and renal vascular hypertension, having a structural formula as follows:

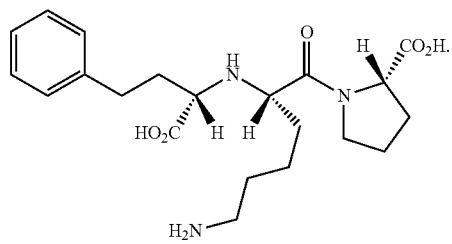 [SMILES: NCCCC[C@H](N[C@@H](CCc1ccccc1)C(=O)O)C(=O)N1CCC[C@H]1C(=O)O]

Lisinopril hydride, with the full name of $N^2$-[1-(S)-ethoxycarbonyl-3-phenylpropyl]-$N^6$-trifluoroacetyl-L-lysine, is an important intermediate for the synthesis of lisinopril, with a structure formula as follows:

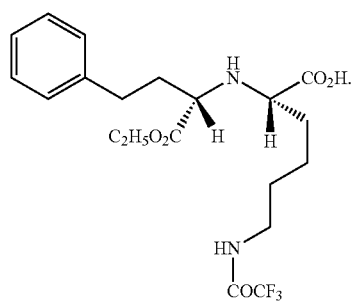

There are mainly two methods for preparing lisinopril hydride:

1. It is reported in U.S. Pat. No. 4,925,969 to use ethyl 4-oxo-4-phenylbut-2-enoate as a starting material, and by the addition with trifluoroacetyl lysinate followed by hydrogenation reduction in the presence of palladium on carbon to obtain lisinopril hydride. The synthesis route is as follows:

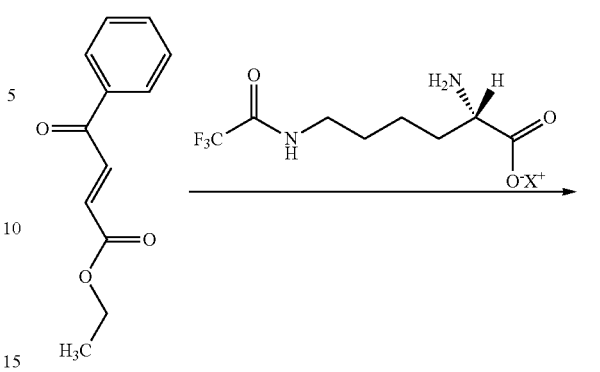

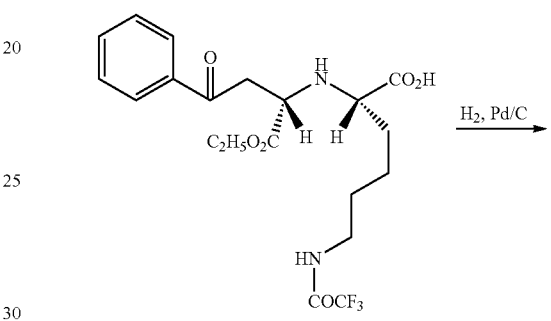

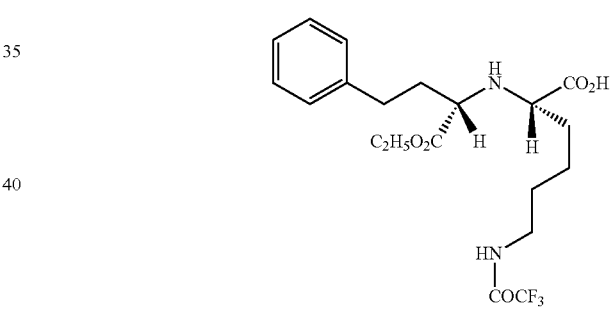

The major problem in this synthesis route is that the adduct isomer is easily produced during the addition, and an isomer of lisinopril hydride is prepared by the hydrogenation reduction of the adduct isomer; the hydrogenation operation requirement and the catalyst cost are high, and impurities can be easily produced.

2. It is reported in WO2005010028 to use the benzyl protected trifluoroacetyl lysine to react with (R)-ethyl 2-trifluoromethylsulfonyloxy-4-phenylbutyrate, and then subject to catalytic hydrogenation in the presence of palladium on carbon to obtain lisinopril hydride.

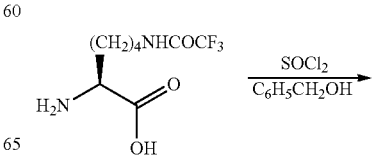

3
-continued

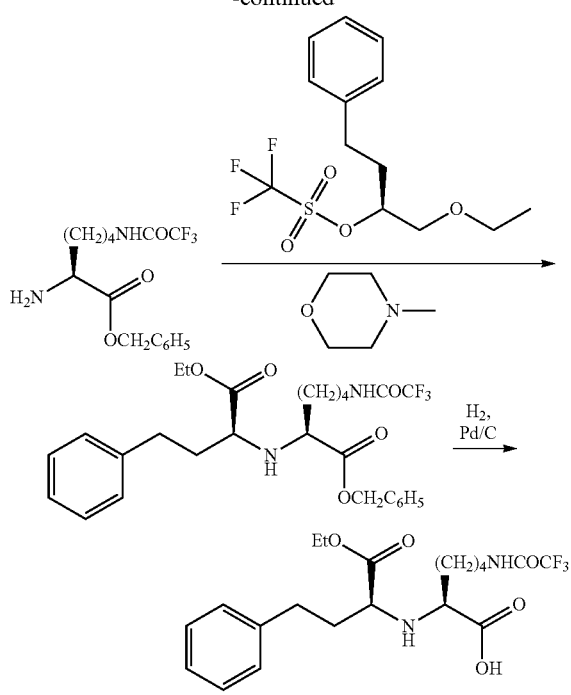

The trifluoroacetyl lysine of the synthesis route needs to be protected by ester formation and then deprotected by hydrogenation, which increases the number of preparation steps and costs.

The preparation methods of lisinopril hydride reported in current literatures have the disadvantages of low yields, high costs, and low atomic utilizations of the routes.

SUMMARY OF THE INVENTION

The object of the present invention is to provide a simple method for preparing $N^2$-[1-(S)-alkoxycarbonyl-3-phenyl-propyl]-$N^6$-trifluoroacetyl-L-lysine (II),

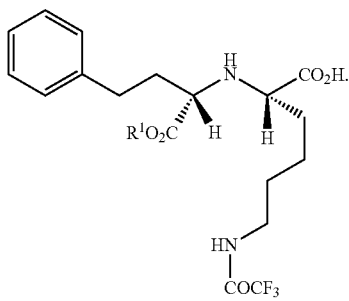
(II)

The method provided by the present invention comprises the following steps:

(a) treating (R)-2-hydroxy-4-phenylbutyrate (I) with a sulfonyl chloride (III) in an organic solvent in the presence of a base to obtain a solution of sulfonate of formula (I);

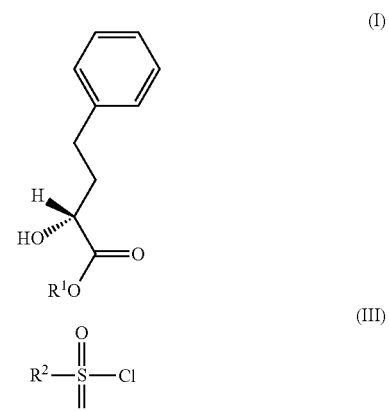

(b) reacting the solution prepared above with a salt of trifluoroacetyl lysine, and obtaining the compound represented by formula (II) by a separation after the reaction is completed, In the above formulas:

$R^1$ is selected from $C_1$-$C_5$ alkyls, and is more preferably methyl, ethyl or isopropyl;

$R^2$ is selected from $C_1$-$C_3$ alkyls or substituted alkyls, $C_6$-$C_7$ aryls or substituted aryls.

The organic solvent described in step (a) is selected from the group consisting of $C_2$-$C_7$ ethers, $C_2$-$C_4$ halogenated alkanes, $C_7$-$C_{10}$ aromatic compounds and a mixed solvent of any two thereof, more preferably: tetrahydrofuran, 2-methyltetrahydrofuran, dichloromethane, toluene, xylene or a mixed solvent of any two thereof. The mass-to-volume ratio of (R)-2-hydroxy-4-phenylbutyrate (I) to the organic solvent is 1 g:2-20 mL, preferably 1 g:5-10 mL.

The base described in step (a) is selected from the group consisting of carbonates or bicarbonates of alkali metals, $C_5$-$C_8$ pyridine compounds, $C_4$-$C_9$ secondary or tertiary amines; more preferably sodium carbonate, potassium carbonate, sodium bicarbonate, pyridine, 2,6-lutidine, triethylamine, diisopropylamine. The molar ratio of the base to (R)-2-hydroxy-4-phenylbutyrate (I) is 1-10:1, preferably 2-4:1.

The sulfonyl chloride described in step (a) is preferably methylsulfonyl chloride, trifluoromethylsulfonyl chloride, p-nitrobenzenesulfonyl chloride or p-toluenesulfonyl chloride. The molar ratio of the sulfonyl chloride to (R)-2-hydroxy-4-phenylbutyrate represented by formula (I) is 1-5:1, preferably 1.1-3:1. The temperature range within which the sulfonyl chloride is added is preferably from −5° C. to 15° C., more preferably from −5° C. to 10° C., still more preferably from 0° C. to 5° C.

The range of the reaction temperature of step (a) is preferably 20-60° C., more preferably 20-40° C., still more preferably 25-35° C.

The reaction time of step (a) is 2-10 hours.

The salt of trifluoroacetyl lysine of step (b) is selected from the group consisting of alkali metal salts of trifluoroacetyl lysine, $C_4$-$C_{12}$ quaternary ammonium salts of trifluoroacetyl lysine, more preferably a lithium salt of trifluoroacetyl lysine, a sodium salt of trifluoroacetyl lysine, a tetramethylammonium salt of trifluoroacetyl lysine. Wherein the molar ratio of the salt of trifluoroacetyl lysine to (R)-2-hydroxy-4-phenylbutyrate (I) is 1-6:1, preferably 1-4:1.

The range of the reaction temperature of step (b) is preferably 10-80° C., more preferably 20-60° C., still more preferably 25-40° C.

The reaction time of step (b) is preferably 1-12 hours.

After the reaction of step (b) is completed, the reaction solvent may be removed, and then the compound of formula (II) is separated and purified in a suitable crystallization solvent, the crystallization solvent is selected from the group consisting of methanol, ethanol, ethyl acetate, isopropyl acetate, methyl tertiary butyl ether, n-hexane, n-heptane, cyclohexane or a mixed solvent of any two thereof; the mass-to-volume ratio of (R)-2-hydroxy-4-phenylbutyrate (I) to the crystallization solvent used is 1 g:2-20 mL, preferably 1 g:4-12 mL; the range of crystallization temperature is preferably from −5° C. to 60° C., more preferably from −5° C. to 40° C., still more preferably from 0° C. to 25° C.; the crystallization time is preferably 5-12 hours.

Furthermore, the process for preparing the compound of formula (II) is as follows:

(a) adding an organic solvent and a base to (R)-2-hydroxy-4-phenylbutyrate (I), slowly adding sulfonyl chloride (III) at −5° C.-15° C., and heating the solution to 20-60° C. and reacting for 2-10 hours under stirring; after the reaction is completed, the reaction solution is filtered;

(b) adding a salt of trifluoroacetyl lysine to the filtrate described above, reacting at 10-80° C. for 1-12 hours under stirring, filtering the reaction solution, and distilling the filtrate under reduced pressure to remove the reaction solvent;

(c) adding a crystallization solvent to the distillation substrate described above, crystallizing at −5° C.-60° C. for 5-12 hours, filtering, and drying the filter cake to obtain a compound of formula (II).

The method for preparing lisinopril hydride and the like thereof provided by the present invention has the advantages of short preparation route, simple and convenient operation, less impurities generated, low cost etc., and is suitable for industrial production.

BRIEF DESCRIPTION OF THE DRAWINGS

FIG. 1 is the HPLC spectrogram of the product, $N^2$-[1-(S)-ethoxycarbonyl-3-phenylpropyl]-$N^6$-trifluoroacetyl-L-lysine, prepared in example 1 of the present application.

EMBODIMENTS

The present invention will be further illustrated by the examples, however, these examples do not constitute any limitation to the present invention.

HPLC instrument model: Shimadzu LC-20A
HPLC conditions:
Chromatographic Column: Agilent Zorbax SB-18 150× 3.0 mm, 3.5 μm;
Mobile phase: 2.5‰ $KH_2PO_4$ solution:acetonitrile=60:40;
Flow rate: 1.0 mL/min, column temperature: 25° C., detection wavelength: 210 nm.

EXAMPLE 1

20.8 g of (R)-ethyl 2-hydroxy-4-phenylbutyrate, 110 mL of dichloromethane and 42.4 g of sodium carbonate were added to a 250 mL three-necked flask, and 26.6 g of p-toluenesulfonyl chloride was slowly added at 0° C. The mixture was heated to 25° C. and reacted under stirring for 8 hours; the reaction solution was filtered, and 62.3 g of a tetramethylammonium salt of trifluoroacetyl lysine was added to the filtrate, and the obtained system reacted under stirring at 15° C. for 10 hours. The reaction solution was filtered, and the filtrate was distilled under reduced pressure to remove dichloromethane. 240 mL of n-hexane was added to the residue and the obtained system was stirred for 5 hours at 0-5° C., 37.2 g of product was obtained, it was determined by HPLC spectrogram that the product was $N^2$-[1-(S)-ethoxycarbonyl-3-phenylpropyl]-$N^6$-trifluoroacetyl-L-lysine, the yield was 86.0%, the HPLC purity was 98.6%, and the HPLC related data are shown in Table 1 below.

TABLE 1

| Peak # | Ret. Time | Area | Height | Area % | Theoretical Plates | Resolution |
|---|---|---|---|---|---|---|
| 1 | 2.595 | 11291 | 930 | 0.071 | 738.127 | 0.000 |
| 2 | 2.912 | 41363 | 3661 | 0.260 | 1742.500 | 0.959 |
| 3 | 4.707 | 3283 | 240 | 0.021 | 1215.483 | 4.383 |
| 4 | 4.931 | 3117 | 222 | 0.020 | 700.093 | 0.348 |
| 5 | 6.109 | 15671095 | 924068 | 98.634 | 3031.845 | 1.982 |
| 6 | 7.317 | 8360 | 652 | 0.053 | 278.804 | 1.099 |
| 7 | 7.654 | 103728 | 4708 | 0.653 | 3036.779 | 0.292 |
| 8 | 11.017 | 32718 | 1141 | 0.206 | 3657.974 | 5.238 |
| 9 | 12.113 | 9111 | 301 | 0.057 | 3951.075 | 1.462 |
| 10 | 13.660 | 4140 | 124 | 0.026 | 4256.754 | 1.924 |
| Total | | 15888206 | 936048 | 100.000 | | |

EXAMPLE 2

20.8 g of (R)-ethyl 2-hydroxy-4-phenylbutyrate, 150 mL of tetrahydrofuran and 20.2 g of triethylamine were added to a 250 mL three-necked flask, and 12.6 g of methylsulfonyl chloride was slowly added at 0° C. The mixture was heated to 25° C. and reacted under stirring for 8 hours; the reaction solution was filtered, and 37.2 g of a lithium salt of trifluoroacetyl lysine was added to the filtrate, and the obtained system reacted under stirring at 25° C. for 10 hours. The reaction solution was filtered, and the filtrate was distilled under reduced pressure to remove tetrahydrofuran. 85 mL of ethanol was added to the residue and the obtained system was stirred for 5 hours at 0° C., 35.9 g $N^2$-[1-(S)-ethoxycarbonyl-3-phenylpropyl]-$N^6$-trifluoroacetyl-L-lysine was obtained, the product showed a HPLC spectrogram that is the same as FIG. 1, the yield was 83.0%, the HPLC purity was 98.9%.

EXAMPLE 3

20.8 g of (R)-ethyl 2-hydroxy-4-phenylbutyrate, 150 mL of tetrahydrofuran and 19.8 g of pyridine were added to a 250 mL three-necked flask, and 13.5 g of methylsulfonyl chloride was slowly added at 0° C. The mixture was heated to 35° C. and reacted under stirring for 6 hours; the reaction solution was filtered, and 39.6 g of a sodium salt of trifluoroacetyl lysine was added to the filtrate, and the obtained system reacted under stirring at 25° C. for 10 hours. The reaction solution was filtered, and the filtrate was distilled under reduced pressure to remove tetrahydrofuran. 40 mL of n-hexane and 200 mL cyclohexane was added to the residue, the obtained system was stirred for 8 hours at 0° C., 36.6 g $N^2$-[1-(S)-ethoxycarbonyl-3-phenylpropyl]-$N^6$-trifluoroacetyl-L-lysine was obtained, the product showed a HPLC spectrogram that is the same as FIG. 1, the yield was 84.7%, the HPLC purity was 98.8%.

EXAMPLE 4

9.7 g of (R)-methyl 2-hydroxy-4-phenylbutyrate, 95 mL of toluene and 20.2 g of triethylamine were added to a 250 mL three-necked flask, and 28.6 g of p-toluenesulfonyl chloride was added at 0° C. The mixture was heated to 35° C. and reacted under stirring for 10 hours; the reaction solution was filtered, and 49.6 g of a lithium salt of trifluoroacetyl lysine was added to the filtrate, and the obtained system reacted under stirring at 40° C. for 12 hours. The reaction solution was filtered, and the filtrate was distilled under reduced pressure to remove toluene. 115 mL of ethyl acetate was added to the residue, the obtained system was stirred for 12 hours at 25° C., 16.4 g $N^2$-[1-(S)-methoxycarbonyl-3-phenylpropyl]-$N^6$-trifluoroacetyl-L-lysine was obtained, the yield was 78.6%, the HPLC purity was 99.1%.

EXAMPLE 5

19.4 g of (R)-methyl 2-hydroxy-4-phenylbutyrate, 160 mL of 2-methyltetrahydrofuran and 33.6 g of sodium bicarbonate were added to a 250 mL three-necked flask, and 18.5 g of trifluoromethylsulfonyl chloride was added at 5° C. The mixture was heated to 25° C. and reacted under stirring for 10 hours; the reaction solution was filtered, and 37.2 g of a lithium salt of trifluoroacetyl lysine was added to the filtrate, and the obtained system reacted under stirring at 30° C. for 12 hours. The reaction solution was filtered, and the filtrate was distilled under reduced pressure to remove 2-methyltetrahydrofuran. 195 mL of n-heptane was added to the residue, the obtained system was stirred for 10 hours at 25° C., 33.8 g $N^2$-[1-(S)-methoxycarbonyl-3-phenylpropyl]-$N^6$-trifluoroacetyl-L-lysine was obtained, the yield was 80.9%, the HPLC purity was 98.1%.

EXAMPLE 6

19.4 g of (R)-methyl 2-hydroxy-4-phenylbutyrate, 160 mL of 2-methyltetrahydrofuran and 26.8 g of 2,6-dimethyl pyridine were added to a 250 mL three-necked flask, and 17.2 g of methyl sulfonyl chloride was added at 0° C. The mixture was heated to 30° C. and reacted under stirring for 7 hours; the reaction solution was filtered, and 37.2 g of a lithium salt of trifluoroacetyl lysine was added to the filtrate, and the obtained system reacted under stirring at 30° C. for 12 hours. The reaction solution was filtered, and the filtrate was distilled under reduced pressure to remove 2-methyltetrahydrofuran. 80 mL of methanol was added to the residue, the obtained system was stirred for 8 hours at 0° C., 35.2 g $N^2$-[1-(S)-methoxycarbonyl-3-phenylpropyl]-$N^6$-trifluoroacetyl-L-lysine was obtained, the yield was 84.2%, the HPLC purity was 98.6%.

EXAMPLE 7

22.2 g of (R)-isopropyl 2-hydroxy-4-phenylbutyrate, 180 mL of dichloromethane and 28.4 g of diisopropylamine were added to a 250 mL three-necked flask, and 28.8 g of p-nitrobenzenesulfonyl chloride was added at 0° C. The mixture was heated to 30° C. and reacted under stirring for 10 hours; the reaction solution was filtered, and 34.6 g of a tetramethylammonium salt of trifluoroacetyl lysine was added to the filtrate, and the obtained system reacted under stirring at 30° C. for 10 hours. The reaction solution was filtered, and the filtrate was distilled under reduced pressure to remove dichloromethane. 100 mL of methyl tertiary butyl ether was added to the residue, the obtained system was stirred for 8 hours at 5° C. to crystallize, filtered, 36.4 g $N^2$-[1-(S)-isopropoxycarbonyl-3-phenylpropyl]-$N^6$-trifluoroacetyl-L-lysine was obtained by drying the filter cake, the yield was 81.4%, the HPLC purity was 98.7%.

EXAMPLE 8

22.2 g of (R)-isopropyl 2-hydroxy-4-phenylbutyrate, 120 mL of tetrahydrofuran and 41.7 g of potassium carbonate were added to a 250 mL three-necked flask, and 28.6 g of p-toluenesulfonyl chloride was added at 10° C. The mixture was heated to 35° C. and reacted under stirring for 8 hours; the reaction solution was filtered, and 37.2 g of a lithium salt of trifluoroacetyl lysine was added to the filtrate, and the obtained system reacted under stirring at 30° C. for 10 hours. The reaction solution was filtered, and the filtrate was distilled under reduced pressure to remove tetrahydrofuran. 200 mL of n-heptane was added to the residue, the obtained system was stirred for 8 hours at 5° C. to crystallize, filtered, 34.3 g $N^2$-[1-(S)-isopropoxycarbonyl-3-phenylpropyl]-$N^6$-trifluoroacetyl-L-lysine was obtained by drying the filter cake, the yield was 76.8%, the HPLC purity was 97.4%.

EXAMPLE 9

20.8 g of (R)-ethyl 2-hydroxy-4-phenylbutyrate, 90 mL of xylene, 60 mL of tetrahydrofuran and 20.0 g of triethylamine were added to a 250 mL three-necked flask, and 13.0 g of methylsulfonyl chloride was added at 0° C. The mixture was heated to 35° C. and reacted under stirring for 8 hours; the reaction solution was filtered, and 37.5 g of a lithium salt of trifluoroacetyl lysine was added to the filtrate, and the obtained system reacted under stirring at 30° C. for 10 hours. The reaction solution was filtered, and the filtrate was distilled under reduced pressure to remove the solvent. 30 mL of isopropyl acetate and 120 mL of n-heptane was added to the residue, the obtained system was stirred for 10 hours at 5° C., 35.5 g $N^2$-[1-(S)-ethoxycarbonyl-3-phenylpropyl]-$N^6$-trifluoroacetyl-L-lysine was obtained, the product showed a HPLC spectrogram that is the same as FIG. 1, the yield was 82.3%, the HPLC purity was 97.5%.

The invention claimed is:
1. A preparation method of $N^2$-[1-(S)-alkoxycarbonyl-3-phenylpropyl]-$N^6$-trifluoroacetyl-L-lysine (II),

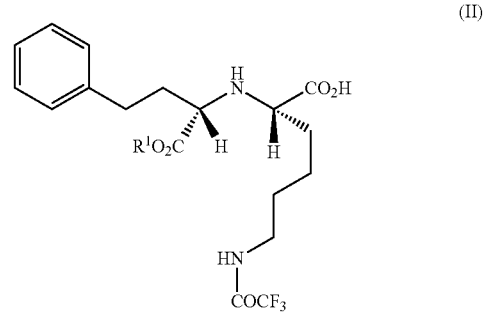

wherein the method comprises the following steps:
(a) treating (R)-2-hydroxy-4-phenylbutyrate (I) with a sulfonyl chloride (III) in an organic solvent in the presence of a base to obtain a solution of sulfonate of formula (I);

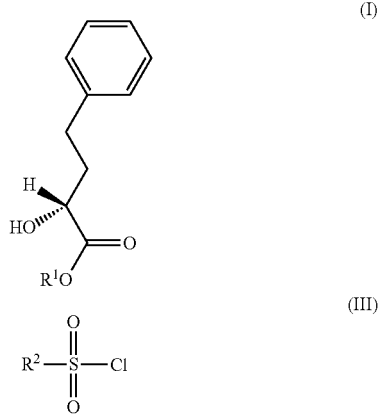

(b) reacting the solution prepared above with a salt of trifluoroacetyl lysine, and obtaining the compound represented by formula (II) by a separation after the reaction is completed, in the above formulas:

$R^1$ is selected from $C_1$-$C_5$ alkyls;

$R^2$ is selected from $C_1$-$C_3$ alkyls or substituted alkyls, $C_6$-$C_7$ aryls or substituted aryls.

2. The preparation method according to claim 1, wherein, $R^1$ is selected from the group consisting of methyl, ethyl and isopropyl.

3. The preparation method according to claim 1, wherein, the organic solvent described in step (a) is selected from the group consisting of $C_2$-$C_7$ ethers, $C_2$-$C_4$ halogenated alkanes, $C_7$-$C_{10}$ aromatic compounds and a mixed solvent of any two thereof.

4. The preparation method according to claim 1, wherein, the mass-to-volume ratio of (R)-2-hydroxy-4-phenylbutyrate (I) to the organic solvent in step (a) is 1 g:2-20 mL.

5. The preparation method according to claim 1, wherein, the base is selected from the group consisting of carbonates or bicarbonates of alkali metals, $C_5$-$C_8$ pyridine compounds, $C_4$-$C_9$ secondary or tertiary amines.

6. The preparation method according to claim 1, wherein, the molar ratio of the base to (R)-2-hydroxy-4-phenylbutyrate (I) is 1-10:1.

7. The preparation method according to claim 1, wherein, the sulfonyl chloride (III) is selected from the group consisting of methylsulfonyl chloride, trifluoromethylsulfonyl chloride, p-nitrobenzenesulfonyl chloride and p-toluenesulfonyl chloride.

8. The preparation method according to claim 1, wherein, the molar ratio of the sulfonyl chloride (III) to (R)-2-hydroxy-4-phenylbutyrate represented by formula (I) is 1-5:1.

9. The preparation method according to claim 1, wherein, the temperature range within which the sulfonyl chloride is added is from −5° C. to 15° C.; the range of the reaction temperature of step (a) is 20-60° C.

10. The preparation method according to claim 1, wherein, the salt of trifluoroacetyl lysine is selected from the group consisting of alkali metal salts of trifluoroacetyl lysine, $C_4$-$C_{12}$ quaternary ammonium salts of trifluoroacetyl lysine.

11. The preparation method according to claim 1, wherein, the molar ratio of the salt of trifluoroacetyl lysine to (R)-2-hydroxy-4-phenylbutyrate (I) is 1-6:1.

12. The preparation method according to claim 1, wherein, the range of the reaction temperature of step (b) is 10-80° C.

13. The preparation method according to claim 1, wherein, the method further comprises crystallizing the crude compound represented by formula (II) obtained by separation in a crystallization solvent, the crystallization solvent is selected from the group consisting of methanol, ethanol, ethyl acetate, isopropyl acetate, methyl tertiary butyl ether, n-hexane, n-heptane, cyclohexane or a mixed solvent of any two thereof; the mass-to-volume ratio of (R)-2-hydroxy-4-phenylbutyrate (I) to the crystallization solvent used is 1 g:2-20 mL; the range of crystallization temperature is from −5° C. to 60° C.

14. The preparation method according to claim 1, wherein, the organic solvent described in step (a) is tetrahydrofuran, 2-methyltetrahydrofuran, dichloromethane, toluene, xylene or a mixed solvent of any two thereof.

15. The preparation method according to claim 1, wherein, the mass-to-volume ratio of (R)-2-hydroxy-4-phenylbutyrate (I) to the organic solvent in step (a) is 1 g: 5-10 mL.

16. The preparation method according to claim 1, wherein, the base is selected from sodium carbonate, potassium carbonate, sodium bicarbonate, pyridine, 2,6-lutidine, triethylamine, diisopropylamine.

17. The preparation method according to claim 1, wherein, the molar ratio of the sulfonyl chloride (III) to (R)-2-hydroxy-4-phenylbutyrate represented by formula (I) is 1.1-3:1.

18. The preparation method according to claim 1, wherein, the temperature range within which the sulfonyl chloride is added is from −5° C. to 10° C.; the range of the reaction temperature of step (a) is 20-40° C.

19. The preparation method according to claim 1, wherein, the salt of trifluoroacetyl lysine is selected from a lithium salt of trifluoroacetyl lysine, a sodium salt of trifluoroacetyl lysine, a tetramethylammonium salt of trifluoroacetyl lysine.

20. The preparation method according to claim 1, wherein, the range of the reaction temperature of step (b) is 20-60° C.

* * * * *